(12) United States Patent
Abrams

(10) Patent No.: US 6,331,184 B1
(45) Date of Patent: Dec. 18, 2001

(54) DETACHABLE COVERING FOR AN IMPLANTABLE MEDICAL DEVICE

(75) Inventor: Robert M. Abrams, Encinitas, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/459,143

(22) Filed: Dec. 10, 1999

(51) Int. Cl.[7] .................................................. A61M 29/00
(52) U.S. Cl. ................... 606/200; 604/164.09; 623/1.12
(58) Field of Search .................................. 623/1.11, 1.12, 623/1.32, 1.33; 606/194, 195, 153, 200, 99; 604/164.09

(56) References Cited

U.S. PATENT DOCUMENTS

| | | | |
|---|---|---|---|
| 4,364,392 | 12/1982 | Strother et al. | |
| 5,108,407 | * 4/1992 | Geremia et al. | 606/108 |
| 5,151,105 | * 9/1992 | Kwan-Gett | 623/1.11 |
| 5,171,259 | 12/1992 | Inoue | 606/213 |
| 5,282,824 | * 2/1994 | Gianturco | 623/1.11 |
| 5,334,210 | 8/1994 | Gianturco | 606/151 |
| 5,454,833 | 10/1995 | Boussignac et al. | 606/213 |
| 5,507,757 | 4/1996 | Sauer et al. | 606/144 |
| 5,591,195 | * 1/1997 | Taheri et al. | 606/194 |
| 5,690,667 | 11/1997 | Gia | 606/191 |
| 5,782,860 | 7/1998 | Epstein et al. | 606/213 |
| 5,948,191 | * 9/1999 | Solovay | 606/194 |
| 6,063,112 | * 5/2000 | Sgro | 623/1.11 |

FOREIGN PATENT DOCUMENTS

WO 99/30640    6/1999    (WO) .

* cited by examiner

Primary Examiner—David O. Reip
Assistant Examiner—Julian W. Woo
(74) Attorney, Agent, or Firm—Albert K. Kau

(57) ABSTRACT

An endoprosthesis cover may be attached to the distal end of a delivery device. The cover may be generally cylindrical in shape and may have a lumen through it. An endoprosthesis may then be covered as it is delivered to a treatment site.

13 Claims, 3 Drawing Sheets

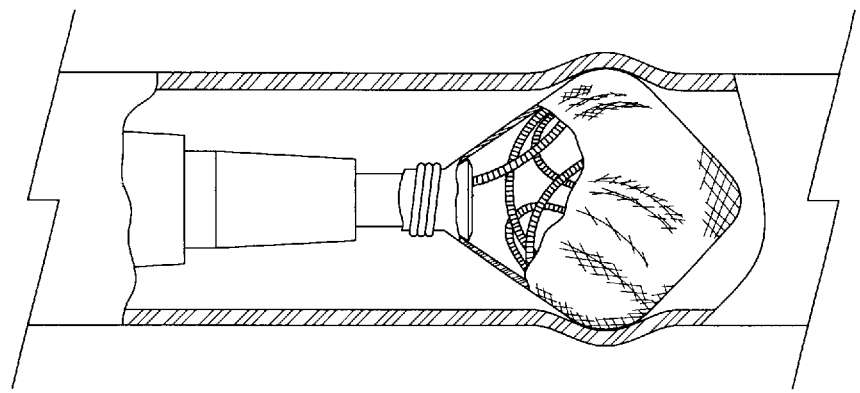
PRIOR ART FIG. 1
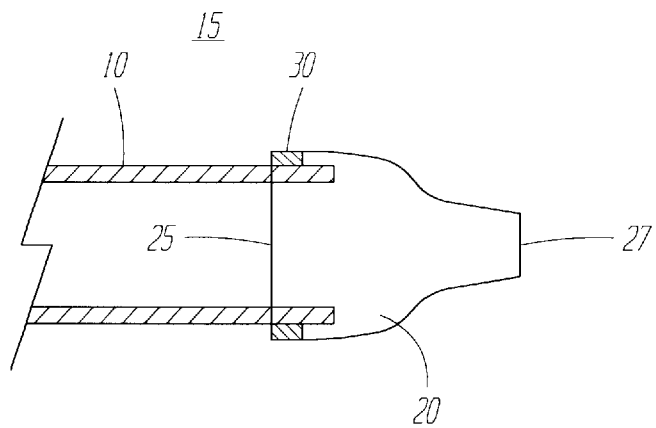
FIG. 2
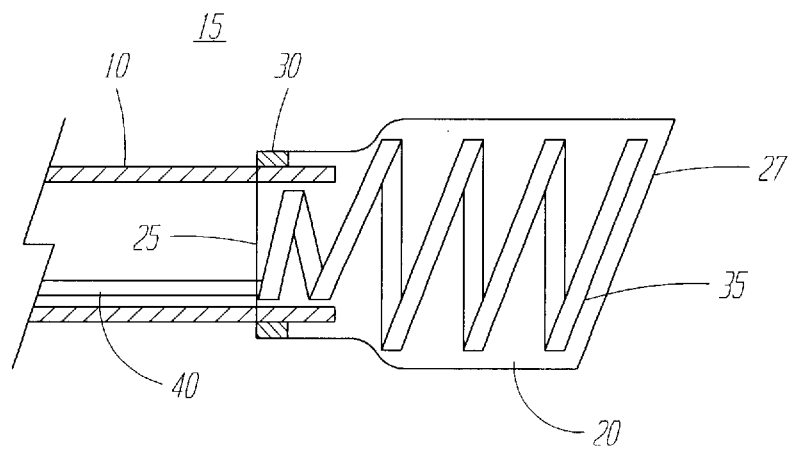
FIG. 3

DETACHABLE COVERING FOR AN IMPLANTABLE MEDICAL DEVICE

FIELD OF THE INVENTION

The present invention generally relates to devices implanted within the human body and further to coverings about those devices. Specifically, the present invention relates to a detachable system for covering an implantable devices as it is delivered into the human body. Those skilled in the art will recognize the benefits of applying the present invention to similar fields not discussed herein.

BACKGROUND OF THE INVENTION

A variety of devices are now commercially available for implantation through minimally invasive techniques. These devices include stents and stent-grafts used to maintain patent flow in blood vessels, the endo-biliary system or the urinary system. These stents and stent grafts have several different forms. Some are in the form of coiled wires while others are made from slotted tubes. Stents are also generally self-expanding or balloon expandable. Typically, they are made from metal and have a few important characteristics. These characteristics include expanded hoop strength, expansion force, expanded and unexpanded diameter, and the amount of foreshortening during expansion. Obviously the art of stent design is to work with these conflicting characteristics in such a way as to form the ideal stent. That stent would require very little force to expand, start with a very small unexpanded diameter and reliably expand to whatever diameter desired and the stent would not foreshorten when expanded.

Another important characteristic of a stent or stent-graft is the amount of expanded stent material that comes into contact with the vessel. Having the surface of the stent in contact with the vessel is important because of in-stent restenosis. In-stent restenosis is a phenomenon where, for some reason, the vessel grows through the struts or between the coils and thereby obstructs fluid flow in the vessel. Where the stent is in direct contact with the vessel, the vessel can not impinge on the fluid flow. There is, therefore, a need for a stent which maximizes all of the characteristics above and has as close to 100% vessel contact in the area that is stented as possible.

Another type of device may generally be characterized as aneurysm repair devices. Depending upon where in the body the aneurysm is located, a ruptured aneurysm may be fatal. Typically aneurysm repair devices are used to prevent the aneurysm from getting larger and ultimately bursting. Exemplary types of aneurysm repair devices include those which protect the aneurysm from getting larger by shielding the aneurysm from fluid pressure, covering the neck of an aneurysm, or filling the aneurysm with some sort of packing material. Similar to stents, aneurysm repair devices have a variety of conflicting material characteristics which make them perform better, most notably surface contact or sealing capability. In addition, present coil-shaped repair devices have a potential for the leading edge of the coil to corkscrew into the vessel wall. There is therefore a need for an aneurysm repair device that has good sealing characteristics and one which would be less likely to corkscrew into the vessel wall.

U.S. Pat. No. 5,334,210 describes a prior art vascular occlusion assembly and is depicted in FIG. 1 of the current application. The assembly comprises a foldable material occlusion bag which is filled with a flexible filler. Because the material is not non-compliant, it must be folded and must therefore disadvantageously increase the profile of the device. This bag may be positioned in a blood vessel and is intended to stop fluid from flowing through the vessel. There is therefore no lumen in the device.

Overall there is need for a prosthesis which has nearly complete vessel wall contact while maintaining a patent fluid channel. This prosthesis and its accompanying delivery system would be highly advantageous.

SUMMARY OF THE INVENTION

The present invention overcomes the deficiencies of the prior art by providing a sheath attached to the distal end of a delivery device. The sheath may be generally cylindrical in shape and have a lumen therethrough. The sheath may be expandable such that, as an endoprosthesis is delivered into the lumen of the sheath, the sheath will take on the exterior configuration of the endoprosthesis. The endoprosthesis is thereby covered while maintaining a patent fluid lumen. The sheath may further be detachable from the delivery device and may have holes or slots to enhance blood porosity and to enhance its distensability. The endoprosthesis may include stents, coils, stent grafts, aneurysm repair devices or any other endoprosthesis known in the art.

BRIEF DESCRIPTION OF THE DRAWINGS

FIG. 1 depicts a prior art device.

FIG. 2 illustrates a first embodiment of the delivery system.

FIG. 3 depicts a partially deployed coil with the delivery system.

DETAILED DESCRIPTION OF THE INVENTION

Figure 4:
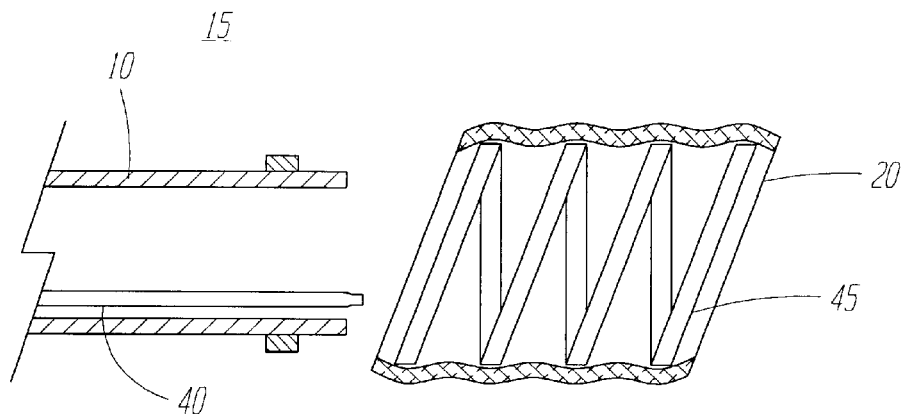
FIG. 4 depicts a fully deployed stent in a body lumen.

The following detailed description should be read with reference to the drawings in which like elements in different drawing are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

Turning now to FIG. 2. Delivery system 15 includes tube 10. Tube 10 may be a micro-catheter, guide catheter, hypotube or any other type of tube commonly known in the art. Depending on the application, the inner diameter or tube 10 may be 0.008–0.39 inches. Tube 10 may be formed of a polymer or a combination of polymers, metal, a metal polymer composite, a combination of polymers and metallic braid (not shown). Surrounding a distal portion of tube 10 is sheath 20. Sheath 20 may preferably be made of an elastomer or other highly compliant polymer. Such polymers may include latex, styrenic block copolymers such as SBS and SEBS made by Shell under trade name of Kraton, polyether-ester block copolymers (COPE) for co-polyesters made by DuPont under the trade name of Hytrel, thermoplastic polyamide elastomers (PEBA) made by Atochem under the trade name of Pebax, and thermoplastic polyurethane elastomer (TPUR) made by Dow under the trade name Pellathane, or thermoplastic polyolefin elastomers (TPOs).

Sheath 20 may further include a proximal opening 25 and a distal opening 27. In its non-distended configuration, sheath 20 may generally form a cylinder. Sheath 20 may have a ridge (not shown) on its interior near distal opening 27 which may be configured to better capture the distal end of a prosthesis. In an alternative embodiment, sheath 20 my have slots or holes (not shown) which would enhance the porosity of sheath 20 and provide better flexibility.

Sheath 20 may be frictionally fit about the distal end of tube 10. In a preferred embodiment, an adhesive bond 30 binds sheath 20 to tube 10. Sheath 20 may detach from tube 10 in a variety of ways. Where sheath 20 is frictionally fit over tube 10, detachment may be achieved simply by overcoming the frictional forces between sheath 20 and tube 10, e.g. pushing a prosthesis out of the distal end of tube 10. Where sheath 20 is attached to tube 10 by adhesive bond 30, the adhesive may be engineered to detach at any desired force. Adhesive bond 30 may be formed with any medically approved adhesive. In an alternative embodiment, sheath 20 may have a circumferential perforation distal of adhesive bond 30 and thereby provide sheath 20 with a tear away detachment mechanism.

Turning now to FIG. 3. Delivery system 15 is shown with a partially deployed self expanding coil 35. Coil 35 may be attached to pusher wire 40. When pusher wire 40 is moved distally relative to tube 10, the distal portion of coil 35 engages the distal portion of sheath 20. Sheath 20 then distends distally has coil 35 is advanced further out of tube 10. Once the entire coil 35 has been pushed out of tube 10, pusher wire 40 may be electrolytically detached. Methods of electrolytic detach are describe in U.S. Pat. No. 5,122,136 which is hereby incorporated by reference. It may further be appreciated that a variety of detach mechanisms are available to serve this function and furthermore that pusher wire 40 does not need to be attached to coil 35.

Figure 5:
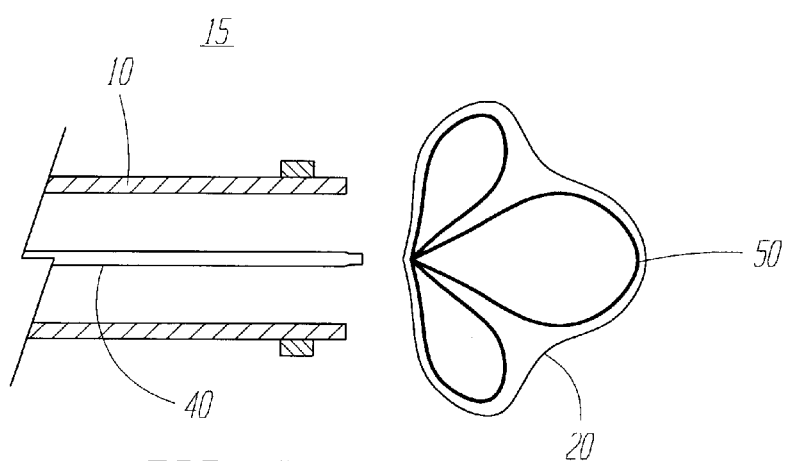
FIG. 5 illustrates a second endoprosthesis.

FIG. 4 depicts delivery system 15 in use in the vasculature. In this embodiment, a self-expanding stent 45 has been introduced into a blood vessel. Pusher 40 has been advanced such that stent 45 was forced out of tube 10 and into contact with the interior of sheath 20. After sheath 20 detached from tube 10, sheath 20 remains in place about stent 45 and prevents any incursion by the surrounding tissue into the lumen of stent 45 and thereby maintains a patent fluid lumen for blood to flow through. Another embodiment is depicted in FIG. 5 where a tulip shaped coil 50 is placed in a body lumen.

Figure 6:
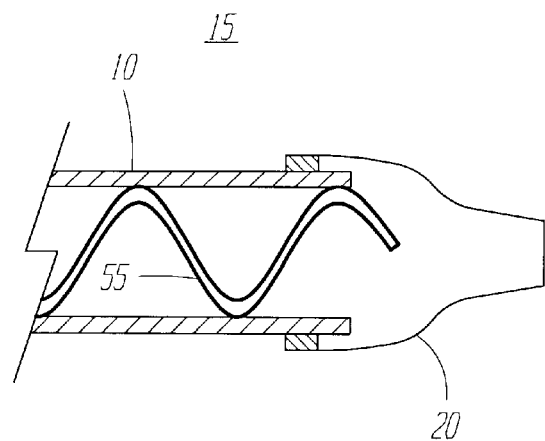
FIG. 6 illustrates a third endoprosthesis.

FIG. 6 illustrates yet another embodiment where wire 55 is advanced through tube 10. Wire 55 may be formed of any suitable medically approved metal such as stainless steel or alloys of nickel such as Nitinol. Wire 55 has a pre-curved shape and is only forced out of that shape by placing wire 55 into tube 10. Care should be taken to choose a material for sheath 20 which will conform to the pre-curved shape of wire 55 without deforming wire 55.

Figure 7:
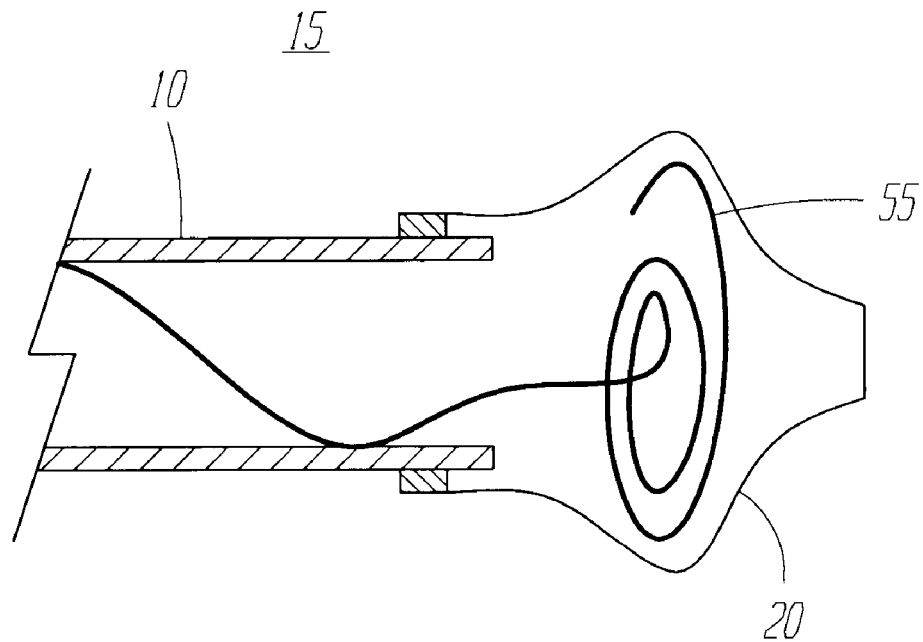
FIG. 7 depicts the third endoprosthesis partially deployed.
Figure 8:
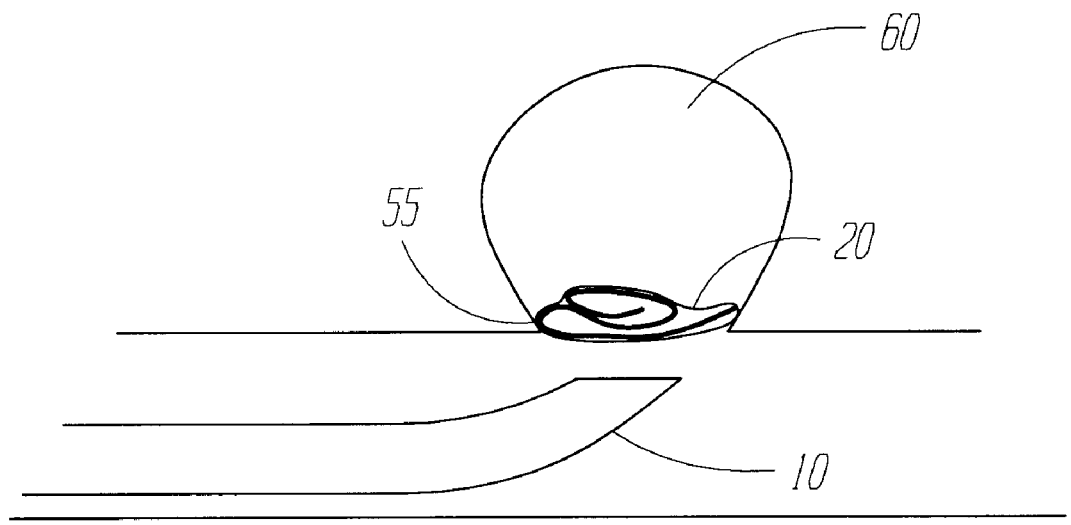
FIG. 8 illustrates the third endoprosthesis fully deployed in an aneurysm neck.

As can readily be appreciated from FIG. 7, as wire 55 emerges from tube 10 it enters sheath 20 and resumes its pre-curved shape. In this embodiment, wire 55 is pre-curved into a flat disc-like shape but could be any of a variety of shapes known in the art. As described above, further advancement of wire 55 eventually detaches sheath 20 from tube 10 and thereby delivers pre-curved wire 55 into a desired location with sheath 20 surrounding wire 55. FIG. 8 depicts a particular use of pre-curved wire 55. In this embodiment wire 55 forms into a disc-like shape suitable for covering an aneurysm neck. Wire 55 may be delivered without any other structure being placed into aneurysm 60. Alternatively, wire 55 may be delivered after particles or other embolic materials (not shown) have been deployed into aneurysm 60. In another embodiment wire 55 may be delivered into aneurysm 60 and particles may be delivered through wire 55 thereby filling aneurysm 60 and capping it with wire 55.

While the specification describes the preferred designs, materials, methods of manufacture and methods of use, those skilled in the art will appreciate the scope and spirit of the invention with reference to the appended claims.

I claim:

1. A device for delivering an expandable prosthesis in a body lumen comprising:

an elongate body having a distal end and a lumen therethrough, the expandable prosthesis at least partially within the lumen; and an expandable sheath releasably attached to the distal end of the body, the sheath having a distal opening and a lumen therethrough, the sheath further configured to receive the expandable prosthesis and at least a portion of the sheath surrounding the elongate body.

2. The sheath of claim 1 wherein the releasable attachment comprises an adhesive calibrated to detach from the elongate body when a sufficient expansion force is applied to the sheath by the expandable prosthesis.

3. The sheath of claim 1 wherein the releasable attachment comprises a circumferential perforation configured to detach from the elongate body when a sufficient expansion force is applied to the sheath by the expandable prosthesis.

4. The sheath of claim 1 further comprising perforations to allow blood porosity and to enhance distensability.

5. The expandable prosthesis of claim 1 comprising a stent.

6. The expandable prosthesis of claim 1 comprising a coil.

7. A detachable prosthesis cover comprising:

a tubular member;

a prosthesis located at least partially within a lumen of the tubular member; and a generally tubular sheath having a lumen therethrough, a proximal region of the sheath circumferentially surrounding a distal end of the tubular member, and a distal region of the sheath having an opening the sheath configured to capture the prosthesis delivered from the tubular member into the lumen of the sheath and the sheath further configured to separate from the tubular member.

8. The prosthesis of claim 7 comprising a stent.

9. The prosthesis of claim 7 comprising a coil.

10. A method of delivering a prosthesis comprising:

providing a delivery system comprising a tubular member, a tubular sheath having a proximal end releasably affixed to the exterior of the tubular member and an opening at a distal end, a prosthesis at least partially positioned with the tubular member, and an actuator for deploying the prosthesis;

advancing a distal end of the tubular member through a body vessel to a position within a human body; and deploying the prosthesis such that the sheath is positioned between the prosthesis and a vessel wall while maintaining a patent fluid path through the vessel.

11. The method of claim 10 further comprising detaching the sheath from the tubular member as the prosthesis is deployed.

12. The method of claim 11 wherein the prosthesis is deployed in an aneurysm neck.

13. The method of claim 10 wherein the prosthesis is deployed in an aneurysm.

\* \* \* \* \*